United States Patent
Fengler et al.

(10) Patent No.: US 9,173,554 B2
(45) Date of Patent: Nov. 3, 2015

(54) IMAGING SYSTEM FOR COMBINED FULL-COLOR REFLECTANCE AND NEAR-INFRARED IMAGING

(75) Inventors: John Fengler, North Vancouver (CA); Paul Westwick, Vancouver (CA); Arthur E. Bailey, North Vancouver (CA); Paul Cottle, Vancouver (CA)

(73) Assignee: NOVADAQ TECHNOLOGIES, INC., Mississauga (CA)

( * ) Notice: Subject to any disclaimer, the term of this patent is extended or adjusted under 35 U.S.C. 154(b) by 1240 days.

(21) Appl. No.: 12/933,512

(22) PCT Filed: Mar. 18, 2009

(86) PCT No.: PCT/US2009/037506
§ 371 (c)(1),
(2), (4) Date: Nov. 24, 2010

(87) PCT Pub. No.: WO2009/117483
PCT Pub. Date: Sep. 24, 2009

(65) Prior Publication Data
US 2011/0063427 A1    Mar. 17, 2011

Related U.S. Application Data

(60) Provisional application No. 61/037,514, filed on Mar. 18, 2008.

(51) Int. Cl.
*A61B 1/04* (2006.01)
*A61B 1/00* (2006.01)
(Continued)

(52) U.S. Cl.
CPC .............. *A61B 1/043* (2013.01); *A61B 1/0005* (2013.01); *A61B 1/00186* (2013.01); *A61B 1/04* (2013.01);
(Continued)

(58) Field of Classification Search
CPC ........ A61B 1/0638; A61B 1/043; A61B 1/06; A61B 1/0646
See application file for complete search history.

(56) References Cited

U.S. PATENT DOCUMENTS 4,717,952 A * 1/1988 Kohayakawa et al. ........ 348/164
5,515,449 A * 5/1996 Tsuruoka et al. .............. 382/128
(Continued)

FOREIGN PATENT DOCUMENTS

JP    A-02-049302    2/1990
JP    10-201707 A    8/1998
(Continued)

OTHER PUBLICATIONS

Int'l Preliminary Report on Patentablility, PCT/US2009/037506 (Sep. 21, 2010).*

(Continued)

*Primary Examiner* — David N Werner
(74) *Attorney, Agent, or Firm* — Oliff PLC (57) ABSTRACT

An imaging system for acquisition of NIR and full-color images includes a light source providing visible light and NIR light to an area under observation, such as living tissue, a camera having one or more image sensors configured to separately detect blue reflectance light, green reflectance light, and combined red reflectance light/detected NIR light returned from the area under observation. A controller in signal communication with the light source and the camera is configured to control the light source to continuously illuminate area under observation with temporally continuous blue/green illumination light and with red illumination light and NIR excitation light. At least one of the red illumination light and NIR excitation light are switched on and off periodically in synchronism with the acquisition of red and NIR light images in the camera.

29 Claims, 8 Drawing Sheets (51) Int. Cl.
*A61B 1/06* (2006.01)
*A61B 5/00* (2006.01)
*A61B 1/045* (2006.01)
*H04N 5/33* (2006.01)

(52) U.S. Cl.
CPC ............... *A61B 1/042* (2013.01); *A61B 1/045* (2013.01); *A61B 1/0638* (2013.01); *A61B 1/0646* (2013.01); *A61B 5/418* (2013.01); *A61B 1/00009* (2013.01); *A61B 1/00043* (2013.01); *A61B 1/00045* (2013.01); *A61B 1/00163* (2013.01); *A61B 1/06* (2013.01); *A61B 1/0669* (2013.01); *A61B 5/0062* (2013.01); *A61B 5/0071* (2013.01); *A61B 5/0075* (2013.01); *A61B 5/0086* (2013.01); *G06T 2207/10048* (2013.01); *H04N 5/33* (2013.01); *H04N 5/332* (2013.01)

(56) References Cited

U.S. PATENT DOCUMENTS

| | | | |
|---|---|---|---|
| 6,596,996 | B1 | 7/2003 | Stone et al. |
| 7,179,222 | B2* | 2/2007 | Imaizumi et al. ............ 600/109 |
| 7,253,894 | B2 | 8/2007 | Zeng et al. |
| 8,285,015 | B2* | 10/2012 | Demos ........................ 382/128 |
| 8,498,695 | B2 | 7/2013 | Westwick et al. ............ 600/478 |
| 2002/0013937 | A1* | 1/2002 | Ostanevich et al. ............ 717/9 |
| 2002/0016533 | A1* | 2/2002 | Marchitto et al. ............ 600/310 |
| 2002/0021355 | A1 | 2/2002 | Utsui |
| 2002/0035330 | A1* | 3/2002 | Cline et al. .................... 600/476 |
| 2002/0138008 | A1* | 9/2002 | Tsujita et al. .................. 600/473 |
| 2003/0229270 | A1* | 12/2003 | Suzuki et al. .................. 600/178 |
| 2004/0006276 | A1* | 1/2004 | Demos et al. .................. 600/476 |
| 2004/0044275 | A1* | 3/2004 | Hakamata ...................... 600/310 |
| 2004/0148141 | A1* | 7/2004 | Tsujita et al. .................. 702/190 |
| 2004/0186351 | A1* | 9/2004 | Imaizumi et al. ............. 600/160 |
| 2004/0225222 | A1 | 11/2004 | Zeng et al. |
| 2004/0245350 | A1* | 12/2004 | Zeng ................................ 236/43 |
| 2004/0263643 | A1* | 12/2004 | Imaizumi et al. ........... 348/222.1 |
| 2005/0171440 | A1 | 8/2005 | Maki et al. |
| 2005/0182321 | A1* | 8/2005 | Frangioni ...................... 600/431 |
| 2005/0203421 | A1 | 9/2005 | Zeng |
| 2006/0155166 | A1* | 7/2006 | Takahashi et al. ............ 600/109 |
| 2007/0213593 | A1* | 9/2007 | Nakaoka ........................ 600/181 |
| 2007/0229309 | A1* | 10/2007 | Tomita et al. .................. 340/992 |
| 2008/0039697 | A1* | 2/2008 | Morishita ...................... 600/181 |
| 2008/0177140 | A1* | 7/2008 | Cline et al. .................... 600/112 |
| 2009/0021739 | A1* | 1/2009 | Tsujita et al. .................. 356/407 |
| 2009/0052185 | A1* | 2/2009 | Toriyama et al. ............. 362/293 |
| 2009/0181339 | A1* | 7/2009 | Liang et al. ..................... 433/29 |
| 2010/0094136 | A1* | 4/2010 | Nakaoka et al. ............... 600/477 |
| 2010/0157039 | A1* | 6/2010 | Sugai ............................... 348/68 |

FOREIGN PATENT DOCUMENTS

| | | |
|---|---|---|
| JP | 2002-000560 A | 1/2002 |
| JP | 2004-520105 A | 7/2004 |
| JP | 2004-289545 A | 10/2004 |
| JP | 2006-525494 A | 11/2006 |
| JP | A-2007-029453 | 2/2007 |
| JP | A-2007-089840 | 4/2007 |
| JP | A-2011-500921 | 1/2011 |
| JP | A-2011-528918 | 12/2011 |
| JP | B2-5231625 | 3/2013 |

OTHER PUBLICATIONS

Japanese Office Action dated Apr. 20, 2012, issued in counterpart Japanese Application No. 2011-500921.
Japanese Patent Office, Office Action mailed May 26, 2014 in Japanese Patent Application No. 2013-058356 w/Concise Explanation of the Relevance.
Apr. 3, 2015 Office Action issued in Japanese Application No. 2013-058356.

* cited by examiner

Fig 4 Interlaced Read-out Scheme

Fig 5 Progressive Scan Scheme

Fig 6 Interlaced, with continuous NIR Scheme

IMAGING SYSTEM FOR COMBINED FULL-COLOR REFLECTANCE AND NEAR-INFRARED IMAGING

CROSS-REFERENCE TO RELATED APPLICATIONS

This application is filed under 35 U.S.C. §371 as a U.S. national phase application of PCT/US2009/037506, designating the United States and having an international filing date of Mar. 18, 2009, which claims the benefit of U.S. provisional patent application No. 61/037,514, filed on Mar. 18, 2008, the contents of which are incorporated herein by reference in their entirety.

FIELD OF THE INVENTION

The invention is directed to medical imaging, in particular to a system and method for obtaining visible light images and near infrared light images from an area under observation, such as living tissue, and in particular for use in endoscopy.

BACKGROUND OF THE INVENTION

Near-infrared (NIR) imaging has been described in the literature for various clinical applications. Typically such an imaging modality utilizes a contrast agent (e.g. indocyanine green) that absorbs and/or fluoresces in the NIR. Such contrast agents may be conjugated to targeting molecules (e.g. antibodies) for disease detection. The contrast agents may be introduced into tissue intravenously or subcutaneously to image tissue structure and function (e.g. flow of blood/lymph/bile in vessels) that is not easily seen with standard visible light imaging technology.

Independently of the clinical application, endoscopic NIR imaging devices typically include multiple imaging modes as a practical feature. For example, endoscopists utilize visible spectrum color for both visualization and navigation, and an endoscopic imaging device that offers NIR imaging typically provides a concurrent color image. Such concurrent imaging devices can be realized, for example, as follows:

One conventional configuration utilizes spectral separation of the visible and the NIR light, with full color and NIR image signals acquired using separate sensors for the different color (e.g. red, green, and blue) and NIR spectral bands or a single color sensor with an integrated filter with filter elements transparent to the different spectral bands (e.g. red, green, blue and NIR). Thus, such multi-modality color and NIR imaging devices provide dedicated sensors or sensor pixels for each of the two imaging modes. Disadvantageously, this increases the number of image sensors in multi-sensor implementations or compromises image resolution when on the same sensor, specific sensor pixels are dedicated for NIR imaging while others are utilized for color imaging.

Another conventional configuration utilizes a single monochrome image sensor for sequential imaging of the visible and NIR light. The object is hereby sequentially illuminated with light in the red, green, blue and NIR spectral bands, with separate image frames being acquired for each spectral band and composite color and NIR images being generated from the acquired image frames. However, this approach, where image frames are acquired sequentially at different times, can generate objectionable motion artifacts (i.e. color fringing and "rainbow effects") in the composite color and NIR images. These artifacts can be mitigated by increasing the acquisition or frame rate to more than, for example, 15 frames/second (fps), for example to 90 fps, or even 180 fps. Because of the high data transfer rate, high frame rates are difficult to implement for high definition images (e.g. 2 million pixels), or images having a large dynamic range (>10 bits), thus limiting image size and/or resolution.

It would therefore be desirable to provide a system and a method for simultaneous acquisition of full-color visible light and NIR light images, which obviates the aforementioned disadvantages and does not compromise image resolution and/or introduce objectionable motion artifacts.

SUMMARY OF THE INVENTION

According to one aspect of the invention, a method for acquisition of NIR images and full-color images includes the steps of illuminating an area under observation with continuous blue/green light, and illuminating the area under observation with red light and NIR light, wherein at least one of the red light and NIR light are switched on and off periodically. The blue, green, red and NIR light returning from the area under observation is directed to one or more sensors which are configured to separately detect the blue light, the green light, and the combined red light/NIR light. The red light spectral component and the NIR light spectral component are determined separately from image signals of the combined red light/NIR light, in synchronism with the switched red and NIR light. A full-color reflectance image of the area under observation is rendered and displayed from the blue, green, and red light and an NIR image is likewise rendered and displayed from the NIR light.

According to another aspect of the invention, an imaging system for acquisition of NIR and full-color images includes a light source providing visible light and NIR light to an area under observation, a camera having one or more image sensors configured to separately detect blue and green light, and combined red and NIR light returned from the area under observation, and a controller in signal communication with the light source and the camera. The controller is configured to control the light source to continuously illuminate tissue with blue/green light and to illuminate the area under observation with red light and NIR light, wherein at least one of the red light and NIR light are switched on and off periodically in synchronism with the acquisition of the red and NIR images in the camera.

The controller is further configured to determine from sensor signals representing the combined red light and NIR light separately the red light spectral component and the NIR light spectral component. The imaging system further includes a display receiving image signals corresponding to the blue light, the green light, and the separately determined red light spectral component and rendering therefrom a full-color visible light image of the area under observation. The display also receives the separately determined NIR light spectral component and renders therefrom an NIR image of the area under observation.

The video imaging system may use a three-sensor color camera configured to continuously image the blue and green wavebands and intermittently image the red waveband, thus providing continuous, high quality luma information and a sufficiently continuous complete chroma to produce high quality video images of the area under observation, such as living tissue. In such a configuration, the red image sensor can be time-multiplexed to acquire both red and NIR images (i.e. the red image sensor alternately, and in rapid succession, images both red light for the color information required for the color image and NIR light for image information required for the NIR image). Such time-multiplexing may be coupled to (and synchronized with) the illumination source used to provide the NIR illumination (excitation for fluorescence) and the red light for color imaging. Image processing is then utilized to separate and process the resulting image signals appropriately.

Embodiments of the invention may include one or more of the following features. The area under observation may be alternatingly illuminated with red light and NIR light, wherein the duration of red light may be different from, preferably longer than, the duration of illumination with NIR light. The illumination may be switched at video field or frame rates.

Fields captured by the image sensor and lacking the red light spectral component or the NIR light spectral component may be interpolated from temporally adjacent image fields that include a corresponding red light spectral component or NIR light spectral component. In one embodiment, the NIR light spectral component obtained in the absence of red light may be subtracted from the combined red light/NIR light to obtain the separate red light spectral component. This is advantageous in particular when the detected NIR signal has an intensity comparable to that of the red signal.

In one embodiment, the light source may include an illuminator emitting a substantially constant intensity of visible light and NIR light over a continuous spectral range, and a plurality of movable filters disposed between the illuminator and the area under observation for transmitting temporally continuous blue/green light and temporally discontinuous red light and NIR light.

In another embodiment, the light source may include an illuminator emitting a substantially constant intensity of visible light and NIR light over a continuous spectral range, first dichroic means for separating the visible light and NIR light into blue/green and red light and NIR light, shutter means for transforming the separated red light and NIR light into temporally discontinuous red light and discontinuous NIR light, and second dichroic means for combining the blue/green light, the temporally discontinuous red light and the temporally discontinuous NIR light for transmission to the area under observation.

In yet another embodiment, the light source may include a first illuminator emitting a substantially constant intensity of green and blue light, a second illuminator producing switched red light, a third illuminator producing switched NIR excitation light, and dichroic means for combining the switched red light and the switched NIR light with the green and blue light for transmission to the area under observation. The switched red light and the NIR light may be produced by interrupting a continuous intensity light beam of the red light and the NIR light by a shutter or chopper. Alternatively, the switched red light and the NIR light may be produced by electrically switching the second illuminator and the third illuminator on and off.

The image sensors may employ an interlaced scan or a progressive scan.

The imaging system may include an endoscope.

BRIEF DESCRIPTION OF THE DRAWINGS

The following figures depict certain illustrative embodiments of the invention which are to be understood as illustrative of the invention and not as limiting in any way.

FIG. 3b shows the optical transmission ranges for the spectral components separated by the dichroic prism of FIG. 3a;

DESCRIPTION OF CERTAIN ILLUSTRATED EMBODIMENTS

Color video images are generally obtained with three-sensor color cameras where separate red, green and blue image sensors provide simultaneous contiguous arrays of red, green and blue pixel information. Full color video images are generated by combining the image information from all three sensors. Color fidelity (i.e. a true color rendition) is extremely important in medical imaging applications and all three sensors are used to provide complete color information.

To understand the relative importance of color and spatial information in video images of human tissue, however, it is useful to consider information in such video images in terms of luma and chroma. Luma refers to the brightness information in the image and it is this information that provides the spatial detail that enables the viewer to recognize shapes. The spatial and temporal resolution of luma is consequently crucial to the perception of video image quality. Chroma refers to the color information in the video image. It is a property of human vision that fine detail variations in the chroma of image features are not easily perceived and that such variations are consequently less critical than fine detail variations in luma, in an overall assessment of image quality. It is for this reason that video encoding of chroma information is often sub-sampled.

In video images of human tissue obtained with visible light, the structural details of the tissue are largely contained in the blue and green wavelength regions of the imaged light. Blue and green light tends to be reflected from the tissue surface, whereas red light tends to be highly scattered within the tissue. As a consequence, there is very little fine structural detail in the red light that reaches the red image sensor. It is also known from color science that human vision receives most of the spatial information from the green portion of the visible spectrum—i.e. green light information contributes disproportionately to the luma. The standard formula for calculating luma from gamma-corrected color components is $Y'=0.2126\ R'+0.7152\ G'+0.0722\ B'$. For this reason, spatial and/or temporal interpolation of the red component of video images of human tissue does not significantly affect perception of fine detail in those images.

Similarly to red light, NIR light tends to be scattered in tissue causing NIR image features to be diffusely, rather than sharply defined. Furthermore, because the NIR image highlights areas of interest (i.e. the areas in which the contrast agent is localized), but does not provide the overall visualization or navigational information, it is desirable for a NIR endoscopic imaging device to provide a continuous color image and either a superimposed or side-by-side display of the NIR image information. In such a display the NIR light would also contribute less to the spatial information presented to observer.

Figure 1:
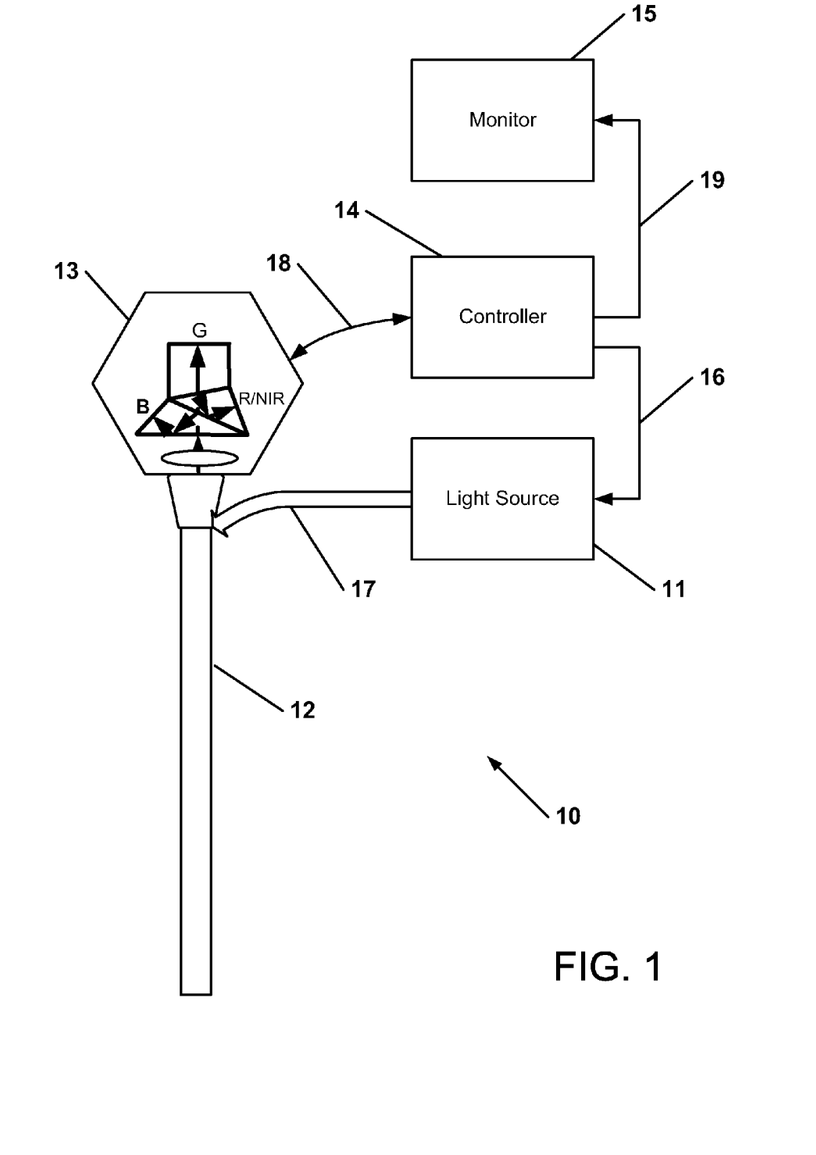
FIG. 1 shows an endoscopic system according to one embodiment of the invention.

FIG. 1 shows schematically an exemplary embodiment of a NIR endoscopic imaging system 10 which includes a multimode light source 11 that provides both visible and NIR illumination, connected to an endoscope 12 by way of an illumination guide, for example a fiber optic cable 17, suitable for transmission of both color and NIR illumination, a color camera 13, illustrated here as having three different sensors 34, 36, 38 (see FIG. 3a) for blue, green and red/NIR imaging, respectively, mounted to the endoscope image guide, and a camera controller 14 connected to the camera 13 and the light source 11 for controlling and synchronizing illumination and image acquisition. Controller 14 can also process the acquired visible and NIR images for display on a monitor 15 connected to the controller 14, for example, by a cable 19. Images can be acquired in real time at selectable frame rates, such as video rates.

FIGS. 2a-2d show schematic diagrams of exemplary embodiments of various light sources 11. The illustrated light sources are constructed to supply in normal color imaging mode visible illumination light yielding a substantially continuous spectral distribution. The light source maybe an arc lamp, a halogen lamp, one or more solid state sources (e.g. LEDs, semiconductor lasers) or any combination thereof and may be spectrally filtered or shaped (e.g. with bandpass filters, IR filters, etc.). The continuous spectrum may be produced as primary colors (RGB) either concurrently or sequentially, for example, using a rotating filter wheel.

In systems according to the present invention, light sources to be used with the system of the invention and described in detail below are configured to provide continuous, uninterrupted illumination in the blue and green parts of the visible spectrum and discontinuous red and/or NIR light. The blue and green parts of the visible spectrum may be optically filtered from the emission produced by a continuous source or produced directly by a narrow-band source (e.g. blue and green LEDs). The red and NIR light may also be produced by an arc lamp, a halogen lamp, a solid state source (e.g., red and NIR LEDs or lasers), or any combination thereof.

Figure 2A:
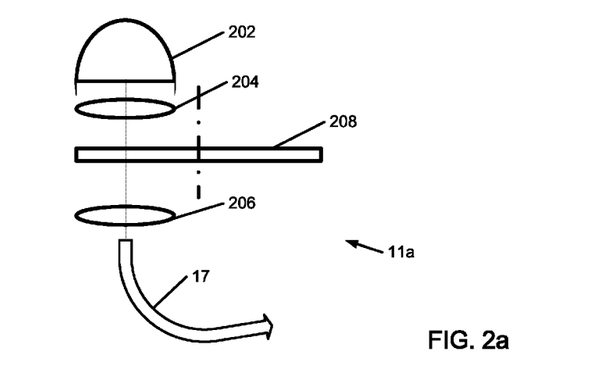
FIGS. 2a-2d show various exemplary embodiments of a multimode light source to be used with the endoscopic system of FIG. 1.

Turning now to FIG. 2a, in one embodiment a light source 11a includes an illuminator 202 producing visible and NIR light emission, a collimating lens 204, a filter wheel or reciprocating filter holder 208 that alternatingly transmits red and NIR light and continuously transmits green and blue light. Alternatively, a tunable electro-optic or acousto-optic filter may be used. The filtered light is focused by lens 206 onto light guide 17.

Figure 2B:
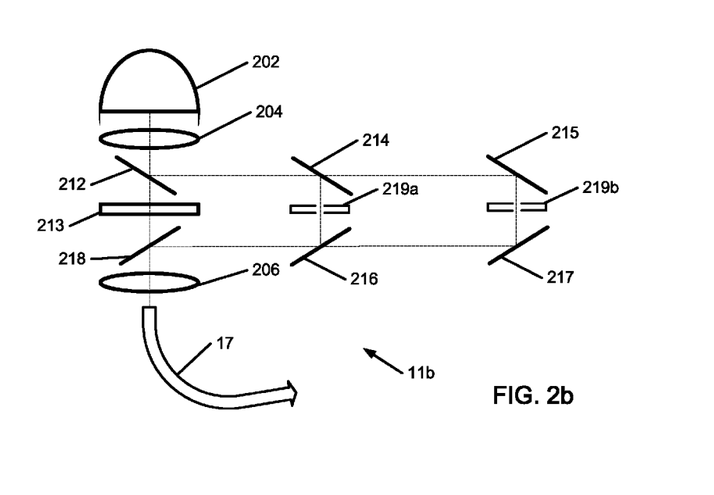

Another embodiment of a light source 11b is schematically illustrated in FIG. 2b. The light source 11b includes an illuminator 202 producing visible and NIR light emission and a collimating lens 204. A dichroic mirror 212 transmits green/blue light and reflects red/NIR light to another dichroic mirror 214 which transmits NIR light to NIR mirror 215 and reflects red light, or vice versa. The green/blue light can be further bandpass-filtered by filter 213. The reflected red and NIR light is chopped, for example, by chopper wheels 219a, 219b (which can be combined into a single chopper wheel) to produce temporally discontinuous illumination, which is then reflected by mirrors 216, 217 and combined with the green/blue light by dichroic mirror 218. The combined light is then focused by lens 206 onto light guide 17, as before.

Figure 2C:
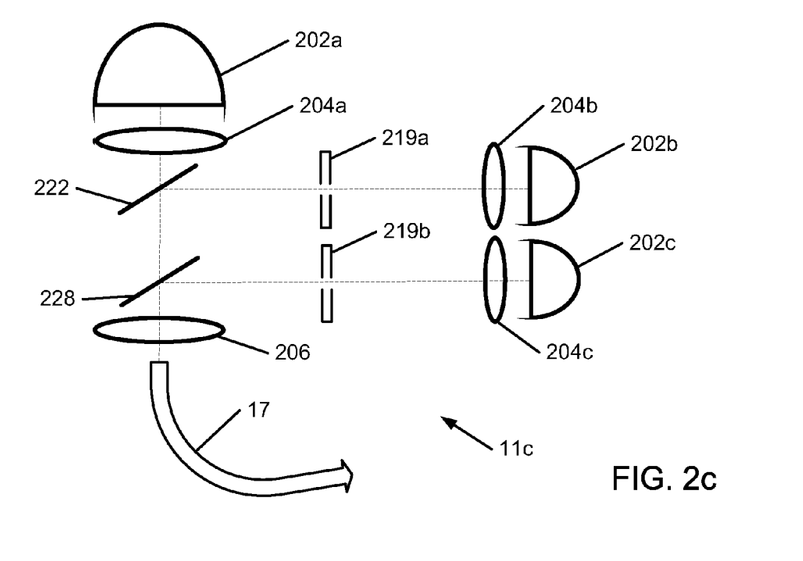

In another embodiment of a light source 11c schematically illustrated in FIG. 2c, an illuminator 202a produces green and blue light emission which is collimated by a collimating lens 204a. Likewise, separate illuminators 202b, 202c produce respective red and NIR light emissions which are collimated by corresponding collimating lenses 204b and 204c. As in the embodiment of FIG. 2b, the red and NIR light is chopped, for example, by chopper wheels 219a, 219b (which may also be combined into a single chopper wheel) to produce temporally discontinuous illumination, which is then combined with the green/blue illumination by dichroic mirrors 222, 228. The combined light is then focused by lens 206 onto light guide 17, as before.

Figure 2D:
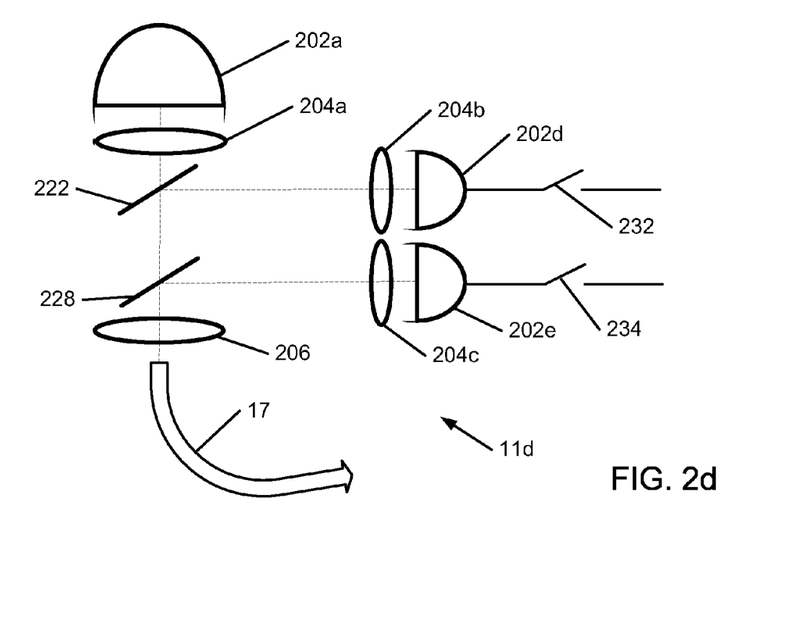

In yet another embodiment of a light source 11d schematically illustrated in FIG. 2d, an illuminator 202a produces green and blue light emission which is collimated by a collimating lens 204a, as before. However, unlike in the embodiment of FIG. 2c, the separate illuminators 202d, 202e are here switched electrically to produce red and NIR light emissions with controlled timing. For example, the red and NIR light sources 202d, 202e may be solid state light sources, such as LEDs or semiconductor lasers, which can be rapidly turned on and off with suitable, preferably electronic, switches. As described above with reference to FIG. 2c, the red and NIR illumination is collimated by corresponding collimating lenses 204b and 204c and combined with the green/blue illumination by dichroic mirrors 222, 228. The combined light is then focused by lens 206 onto light guide 17, as before.

The alternating red and NIR illumination is synchronized with the image acquisition of the three-sensor camera such that red and NIR images are acquired by the camera synchronously with the red and NIR illumination of the endoscope.

Figure 3A:
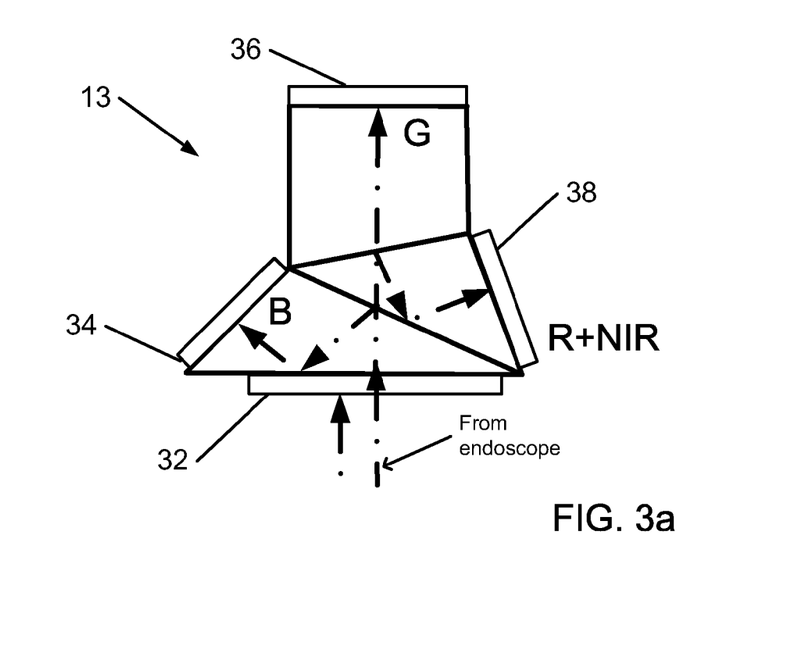
FIG. 3a shows an exemplary dichroic prism employed by a 3-sensor color camera.
Figure 3B:
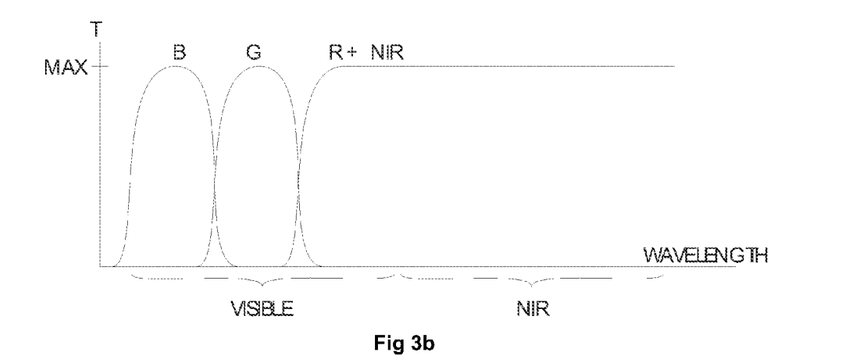
Figure 3C:
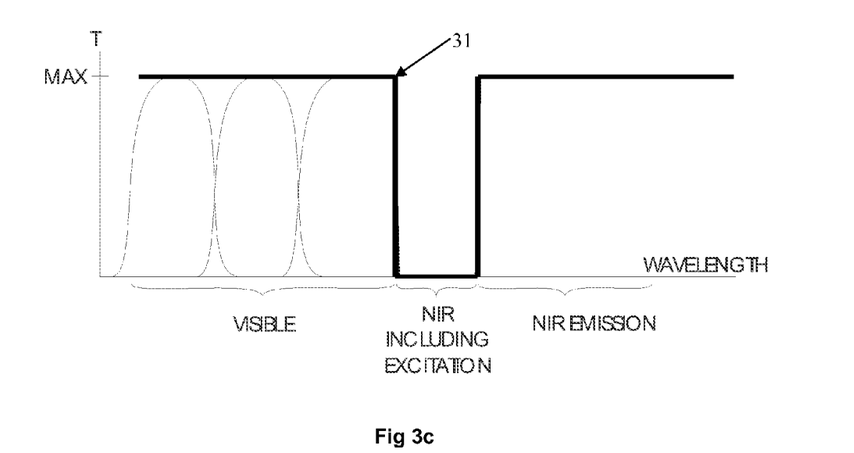
FIG. 3c shows the optical transmission range of a notch filter that blocks excitation light from entering the camera.

FIG. 3a shows in more detail the three-sensor camera 13 of FIG. 1, in particular the optical beam splitter used to direct red/NIR, green, and blue light to the three different image sensors 34, 36 and 38, respectively. For NIR fluorescence applications, the camera preferably also includes an excitation band blocking filter 32. The beam splitter may be made, for example, of a plurality of dichroic prisms, cube splitters, plate splitters or pellicle splitters. FIG. 3b shows the spectral composition of the light received from the endoscope according to FIG. 3a. FIG. 3c illustrates the spectral composition of the light transmitted through the excitation band blocking filter 32 implemented as a notch filter 31 which blocks transmission of excitation light, while transmitting the other wavelengths in the visible and NIR spectral range. The transmission characteristic of this filter 32 may be designed to also block undesired NIR wavelengths interfering with the visible spectrum that may degrade the color image.

Figure 4:
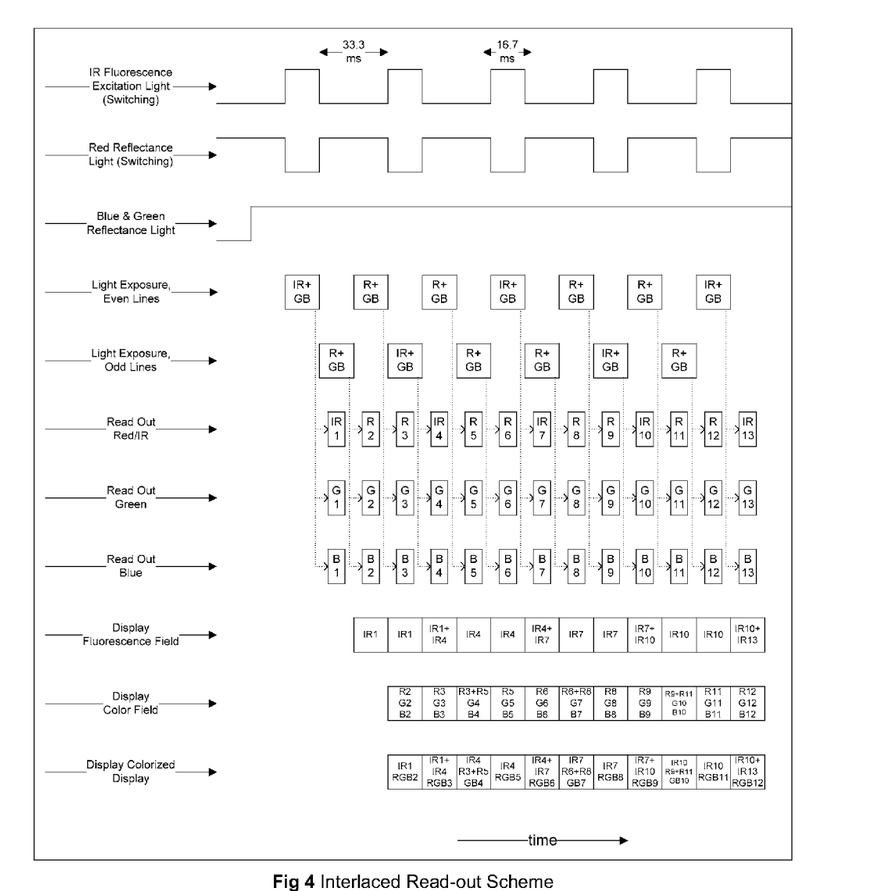
FIG. 4 shows a timing diagram of a first embodiment for continuous illumination with green/blue light and alternating illumination with red/NIR light.

FIG. 4 shows a timing diagram for a first exemplary embodiment of a simultaneous color and NIR imaging mode using, for example, a three-sensor camera. In this embodiment, the camera sensors utilize an interlaced read-out format which represents an advantageous combination of spatial and temporal resolution for smooth display of motion. Any of the light sources illustrated in FIGS. 2a-2d can be used with this embodiment. The light source provides continuous blue/green illumination and alternating red and NIR illumination. Half-frames are alternatingly exposed on the image sensors, i.e., a first field (half-frame) with even lines alternating with a second field (half-frame) with odd lines. In the timing diagram of FIG. 4 depicting a full frame rate of 30 fps, one field period (16.7 ms) provides NIR illumination, followed by two field periods (33.3 ms) of red illumination. Stated differently, the sample or tissue is illuminated with full-spectrum color (RGB) during two field periods (33.3 ms) and with GB and NIR during a third field period. For reconstructing the full-color visible image, the missing red information is interpolated between the fields adjacent to the field with the NIR illumination. The blue and green image information is always available, thereby providing optimum and continuous luma information. The NIR image is generated from every sixth field in each half frame, wherein the missing lines are spatially interpolated. When the fluorescence field is displayed, the image is updated every three fields, with the displayed image interpolated between even and odd lines.

In all the figures, the term "IR" is used instead of or interchangeably with "NIR."

Once the color and NIR image data have been processed, the signal is outputted to a video monitor and may be displayed as two separate, simultaneous views (one color and one fluorescence) or as combined color and fluorescence image signals (e.g. by assigning the fluorescence signal a color that contrasts with the naturally occurring colors in the tissue).

Figure 5:
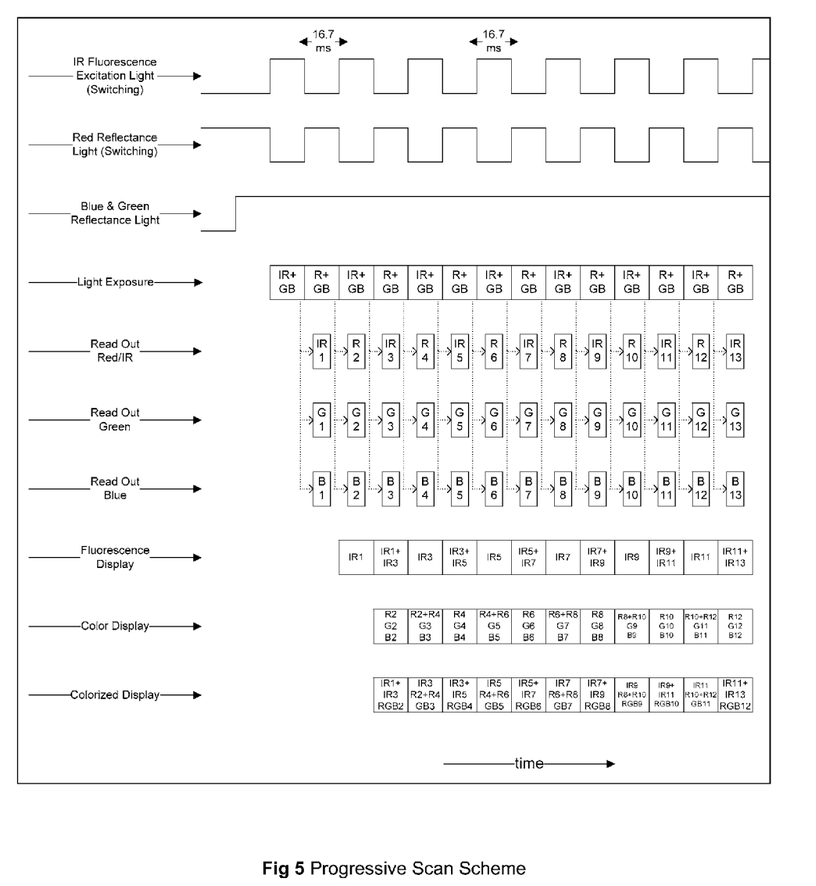
FIG. 5 shows a timing diagram of a second embodiment for continuous illumination with green/blue light and alternating illumination with red/NIR light.

FIG. 5 shows a timing diagram for a second exemplary embodiment of a simultaneous color and NIR imaging mode. In this embodiment, the camera sensors utilize a progressive scan sensor read-out format wherein a complete frame (G/B/R alternating with G/B/NIR) is read out during each field period. Any of the light sources illustrated in FIGS. 2a-2d can be used with this embodiment. The light source provides continuous blue/green illumination and alternating red and NIR illumination. In the timing diagram of FIG. 5, one field period (16.7 ms) provides NIR illumination, followed by one field period (16.7 ms) of red illumination. Stated differently, the sample or tissue is illuminated with full-spectrum color (RGB) during one field period (16.7 ms) and with GB and NIR during a third field period. In this case, a full visible spectrum color image is available at every pixel, in every other frame. In the alternate frames, the blue and green information is acquired directly, whereas the red information is interpolated between adjacent frames. Unlike with the embodiment of FIG. 4, no spatial interpolation is required. Further image processing and display can be implemented in a manner similar to that described in previous embodiments.

Figure 6:
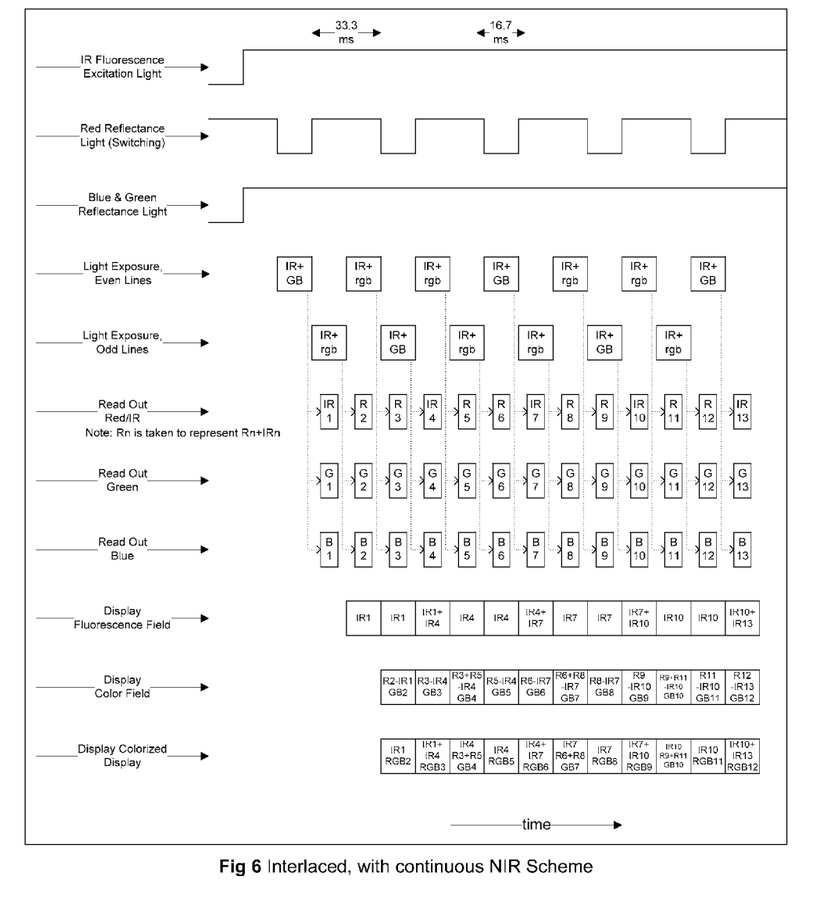
FIG. 6 shows a timing diagram of a third embodiment for continuous illumination with green/blue/NIR light and alternating illumination with red light.

FIG. 6 shows a timing diagram for a third exemplary embodiment, wherein both the green/blue illumination and the NIR illumination are continuous, while only the red illumination is modulated. Like in the embodiment of FIG. 4, half-frames are alternatingly exposed on the image sensors, i.e., a first field (half-frame) with even lines alternating with a second field (half-frame) with odd lines. In the timing diagram of FIG. 6 depicting a full frame rate of 30 fps, one field period (16.7 ms) provides (NIR+GB) illumination (red illumination switched off), followed by two field periods (33.3 ms) of (NIR+RGB). If the NIR image signal is small compared to the red reflected signal, it will not significantly affect the overall visible (RGB) image, so that the color image may be generated by conventional color image processing without correction. Otherwise the NIR contribution obtained in the red image channel when the red illumination is switched off may be subtracted from the (NIR+FR) image data by spatial and temporal interpolation to obtain the red image signal, as shown in the second to last lien in the timing diagram of FIG. 6. Alternatively, sensors with a progressive scan image sensor readout similar to those illustrated in FIG. 5 could be used with RGB and (RGB+IR) image acquisition in alternate frames.

In yet another exemplary embodiment (not illustrated in the drawings), the green/blue illumination as well as the red illumination are continuous, whereas the NIR illumination is modulated. This timing scheme can be best applied if the red and NIR image signals have approximately the same magnitude. In this embodiment, the light source provides uninterrupted illumination with full visible spectrum and intermittent illumination with NIR light. The timing diagram is essentially the same as that depicted in FIG. 6, with the NIR and the red illumination interchanged. The intermittent NIR illumination is synchronized to coincide with every $3^{rd}$ field with interlaced cameras and with every other field in progressive scan cameras. For every field in which NIR illumination is provided, the red image sensor will acquire a (R+NIR) image signal. The NIR image signal can be extracted from the (R+NIR) image signal by interpolation of the red signal value from the appropriate preceding and subsequent "red only" image fields and subtracting the red image signal from the (R+NIR) signal. Since the red and NIR image signals are of similar magnitude, such interpolation and subtraction will provide a reasonably accurate NIR image signal value. The color image is processed by using the acquired and interpolated values for the red image signal in combination with the blue and green image signals. The resulting color and NIR image information can then be displayed or recorded as described before.

In any of the aforementioned embodiments, the NIR endoscopic imaging system can also be operated such that the light sources provides continuous illumination with either the full visible spectrum or the NIR spectrum and the camera acquires the corresponding color image or NIR (absorbance or fluorescence) image in a continuous fashion to provide high spatial resolution. The resulting video image of either individual illumination/imaging mode—color or NIR—can be subsequently displayed and/or recorded.

By implementing color and NIR imaging as described in the aforementioned embodiments, it is possible to acquire and display full-color visible light and NIR light images at video rates without compromising image resolution and/or introducing objectionable motion artifacts. Furthermore, should any residual color fringing occur as a consequence of sharp edges moving rapidly across the visual field (e.g. with the discontinuous acquisition of red or NIR images), these relatively minor effects can be mitigated by temporal interpolation of the missing (red/NIR) video fields with minimum additional processing time.

Figure 7:
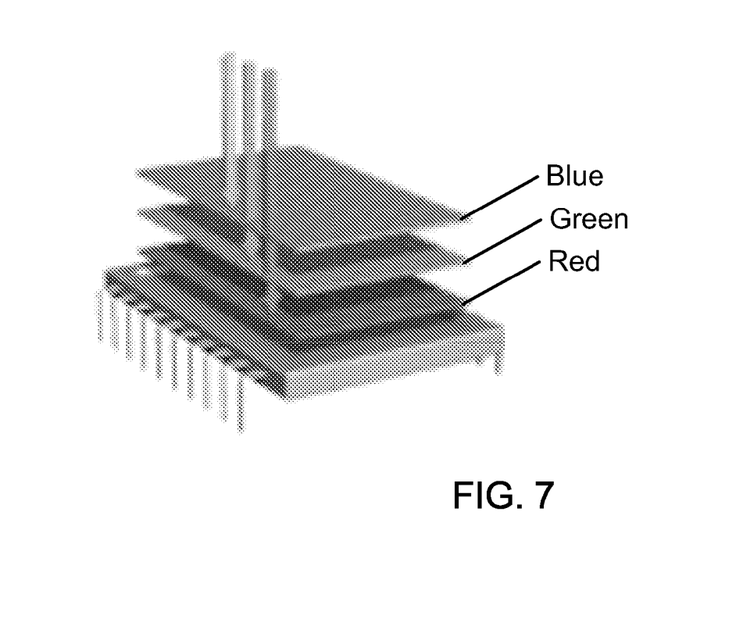
FIG. 7 shows an exemplary CMOS sensor having stacked imaging layers and the corresponding spectral sensitivity of these layers.

While the invention has been disclosed in connection with the preferred embodiments shown and described in detail, various modifications and improvements thereon will become readily apparent to those skilled in the art. For example, instead of using separate image sensors for G/B and R/NIR, or a single color sensor for RGB images and NIR fluorescence images, a single direct three-color RGB sensor image sensor with a stacked pixel design implemented in CMOS technology and commercially available from Foveon, Inc., San Jose, Calif., may be used. Such sensor is schematically illustrated in FIG. 7. It will be understood that this sensor design can be extended to four colors by adding an NIR-sensitive layer. The red, green, blue and NIR images are hereby acquired at different depths in the image sensor. With a 4-layer sensor, multiplexing of the red and NIR illumination would be unnecessary. However, with a 3-layer sensor, the red and NIR illumination would still need to be multiplexed, as described above for a 3-sensor conventional camera. An appropriate barrier filter to block the NIR excitation light would also be required for fluorescence imaging applications.

While the invention has been illustrated and described in connection with currently preferred embodiments shown and described in detail, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

What is claimed is:

1. A method for acquisition of NIR and full-color images, comprising the steps of:
    illuminating a sample area with blue light and green light continuously, and, at the same time, illuminating the sample area with red light and NIR light according to a predetermined timing scheme in which at least one of the red light and the NIR light is switched on and off periodically;
    directing blue reflectance light to a blue light detector, directing green reflectance light to a green light detector, and directing red reflectance light and NIR fluorescence light to a red/NIR light detector, wherein the red reflectance light and/or NIR fluorescence is detected by the red/NIR light detector in synchronism with the predetermined timing scheme;
    simultaneously acquiring first image signals from the blue light detector, second image signals from the green light detector, and third image signals from the red/NIR light detector, the third image signals being multiplexed red light and NIR fluorescence image signals;
    determining from the third image signals and the predetermined timing scheme red reflectance light image signals and NIR fluorescence image signals separate from one another;
    generating a full-color image of the sample area from the first image signals and the second image signals and the separately determined red reflectance light signals;
    generating an NIR image from the separately determined NIR fluorescence image signals; and
    simultaneously displaying the full-color image and the NIR image.

2. The method of claim 1, wherein the sample area is alternatingly illuminated with red light and NIR light.

3. The method of claim 2, wherein a time duration of red light illumination is different from a time duration of NIR light illumination.

4. The method of claim 3, wherein the time duration of red light illumination is longer than the time duration of NIR light illumination.

5. The method of claim 2, wherein a time duration of red light illumination is substantially identical to a time duration of NIR light illumination.

6. The method of claim 1, wherein the sample area is continuously illuminated with red light and periodically illuminated with NIR light.

7. The method of claim 1, wherein the sample area is continuously illuminated with NIR light and periodically illuminated with red light.

8. The method of claim 1, wherein the red light or NIR light, or both, are switched at video rates.

9. The method of claim 2, wherein image fields lacking the red reflectance light spectral component or the detected NIR light spectral component are interpolated from temporally adjacent image fields that include a corresponding red reflectance light spectral component or detected NIR light spectral component.

10. The method of claim 7, wherein the NIR light spectral component obtained in the absence of red light illumination is subtracted from the combined red reflectance light/detected NIR light to obtain the separate red reflectance light spectral component.

11. The method of claim 1, wherein spatial information of the sample area is primarily derived from the blue reflectance light and the green reflectance light.

12. The method of claim 1, wherein the detected NIR light is fluorescence light.

13. The method of claim 1, wherein the step of simultaneously displaying further includes displaying the full-color image and the NIR image in real time.

14. An imaging system for acquisition of NIR images and full-color images comprising:
    a light source providing visible light and NIR light to a sample area;
    a camera having a blue light detector configured to detect blue reflectance light, a green light detector configured to detect green reflectance light, and a red/NIR light detector configured to detect red reflectance light and NIR fluorescence returned from the sample area:
    a controller in signal communication with the light source and the camera for:
        illuminating the sample area with blue light and green light continuously and, at the same time, illuminating the sample area with red light and NIR light according to a predetermined timing scheme in which at least one of the red light and the NIR light is switched on and off periodically,
        simultaneously acquiring first image signals from the blue light detector, second image signals from the green light detector, and third image signals from the red/NIR light detector,
        determining from the third image signals and the predetermined timing scheme the red reflectance light image signals and NIR fluorescence image signals separately from one another, wherein red reflectance light image signals and the NIR fluorescence image signals are determined in synchronism with the switched red light and NIR light; and
    a display receiving the first image signals, the second image signals, and the separately determined red reflectance light image signals of the third image signals and rendering therefrom a full-color reflectance image of the sample area, the display further receiving the separately determined NIR fluorescence image signals of the third image signals and rendering therefrom an NIR image of the sample area.

15. The imaging system of claim 14, wherein the sample area is alternatingly illuminated by the light source with red light and NIR light.

16. The imaging system of claim 14, wherein the light source comprises
    an illuminator emitting a substantially constant intensity of visible light and NIR light over a continuous spectral range, and
    a plurality of filters disposed between the illuminator and the sample area for transmitting temporally continuous blue/green light and temporally discontinuous red light and discontinuous NIR light.

17. The imaging system of claim 14, wherein the light source comprises
    an illuminator emitting a substantially constant intensity of visible light and NIR light over a continuous spectral range, first dichroic means for separating the visible light and NIR light into blue/green and red light and NIR light, shutter means for transforming the separated red light and NIR light into temporally discontinuous red light and discontinuous NIR light, and second dichroic means for combining the blue/green light, the temporally discontinuous red light and the temporally discontinuous NIR light for transmission to the sample area.

18. The imaging system of claim 14, wherein the light source comprises
- a first illuminator emitting a substantially constant intensity of green and blue light,
- a second illuminator producing switched red light,
- a third illuminator producing switched NIR light, and
- dichroic means for combining the switched red light and the switched NIR light with the green and blue light for transmission to the sample area.

19. The imaging system of claim 18, wherein the switched red light and the NIR light are produced by interrupting a continuous intensity light beam of the red light and the NIR light by a shutter or chopper.

20. The imaging system of claim 18, wherein the switched red light and the NIR light are produced by electrically switching the second illuminator and the third illuminator on and off.

21. The imaging system of claim 14, wherein the image sensors employ an interlaced scan.

22. The imaging system of claim 14, wherein the image sensors employ a progressive scan.

23. The imaging system of claim 14, further comprising a dichroic prism assembly spectrally separating the blue reflectance light, the green reflectance light and the combined red reflectance light/detected NIR light returned from the sample area and directing the separated light to different exit faces of the dichroic prism assembly, wherein the one or more image sensors comprise three image sensors, each mounted on a different exit face.

24. The imaging system of claim 14, wherein the one or more image sensors comprise a single image sensor having pixels, each pixel responsive to one of the blue reflectance light, the green reflectance light and the combined red reflectance light/detected NIR light returned from the sample area.

25. The imaging system of claim 24, wherein the single image sensor comprises a mosaic blue/green/red-NIR filter array disposed before the sensor pixels.

26. The imaging system of claim 14, wherein the one or more image sensors comprise a single image sensor having a plurality of stacked layers, each layer having pixels responsive to one of the blue reflectance light, the green reflectance light and the combined red reflectance light/detected NIR light returned from the sample area.

27. The imaging system of claim 14, wherein the imaging system is configured as an endoscope.

28. The imaging system of claim 14, wherein the detected NIR light is fluorescence light.

29. The imaging system of claim 14, wherein the display is configured to render the full-color reflectance image of the sample area and the NIR image of the sample area in real time.

\* \* \* \* \*